United States Patent [19]

Brust

[11] 4,035,416

[45] July 12, 1977

[54] PROCESS FOR MAKING PHENOXYALKANOIC ACIDS

[75] Inventor: Harry F. Brust, Midland, Mich.

[73] Assignee: The Dow Chemical Company, Midland, Mich.

[21] Appl. No.: 303,004

[22] Filed: Nov. 2, 1972

[51] Int. Cl.² .................................. C07C 51/00
[52] U.S. Cl. .................... 260/521 H; 260/521 R
[58] Field of Search ....... 260/521 R, 521 A, 473 G, 260/521 H

[56] References Cited

U.S. PATENT DOCUMENTS

| | | | |
|---|---|---|---|
| 2,480,817 | 8/1949 | Warren | 260/521 A |
| 2,516,611 | 7/1950 | Berhenke et al. | 260/521 A |
| 2,598,692 | 6/1952 | Henrich | 260/521 A |
| 2,599,250 | 6/1952 | Fusco | 260/521 A |
| 2,651,659 | 9/1953 | Warren et al. | 260/521 A |
| 2,656,382 | 10/1953 | Kulka et al. | 260/521 R |
| 2,769,833 | 11/1956 | Weil | 260/521 A |
| 2,866,816 | 12/1958 | Heywood | 260/521 A |
| 3,054,823 | 9/1962 | Toepel | 260/521 R |
| 3,257,453 | 6/1966 | Steinkoenig et al. | 260/521 A |

FOREIGN PATENT DOCUMENTS

| | | | |
|---|---|---|---|
| 592,827 | 9/1947 | United Kingdom | 260/521 A |
| 651,670 | 4/1951 | United Kingdom | 260/521 A |
| 679,676 | 9/1952 | United Kingdom | 260/521 A |
| 723,129 | 2/1955 | United Kingdom | 260/521 A |

*Primary Examiner*—Robert Gerstl
*Attorney, Agent, or Firm*—C. E. Rehberg; L. Wayne White

[57] ABSTRACT

Phenoxyalkanoic acids, e.g., 2,4-dichlorophenoxyacetic acid, are made by simultaneously adding equivalent amounts of haloalkanoic acid and alkali metal hydroxide to a hot mixture of about equimolar amounts of the appropriate phenol and the alkali metal salt of the phenol while distilling water from the reaction mixture as formed.

5 Claims, No Drawings

PROCESS FOR MAKING PHENOXYALKANOIC ACIDS

BACKGROUND OF THE INVENTION

Phenoxyalkanoic acids and their salts and esters are well-known herbicides, especially those wherein the phenyl radical bears halogen substituents. The 2,4-dichloro- and 2,4,5-trichlorophenoxyacetic and -propionic acids and their derivatives are typical examples.

The phenoxyalkanoic acids are usually made by the reaction of an alkali metal salt of the corresponding phenol with an alkali metal salt of the appropriate haloalkanoic acid. These salts are usually made by reaction of the phenol and the acid with alkali metal hydroxide, thus producing water as a by-product. Additionally, water is often used as a solvent for the reaction.

An unavoidable by-product of the above process is hydroxyalkanoic acid. It is formed by the hydrolysis of the haloalkanoic acid and is highly objectionable, both because of the loss of haloalkanoic acid and because of the effort and expense entailed in separating it from the product and from the waste stream of the process. The latter is essentially an aqueous brine and presents a disposal problem. If sufficiently pure, however, it can be electrolyzed to produce halogen and alkali metal hydroxide, both of which can be recycled to the process.

Prior processes have usually attempted to minimize the production of hydroxy acid by minimizing the amount of water present. This has been done by use of a two-phase water-organic reaction medium. U.S. Pat. No. 2,480,817 is typical of this approach.

Another technique involves the use of excess salt of the phenol. To this is added the haloalkanoic acid per se rather than its salt (U.S. Pat. No. 2,651,659).

In still another modification of the above process, excess phenol is used as a liquefying medium in combination with another organic solvent (U.S. Pat. No. 2,656,382). In this process, the amount of water present in the reaction mixture was minimized by using substantially anhydrous reactants. While this process apparently produces high yields, it is tedious and expensive because 1. it requires large volumes of organic solvent,
2. it requires the preparation of anhydrous alkali metal salt of the haloalkanoic acid, and
3. it requires the metering into the reactor of the solid salt or of a slurry thereof in an organic liquid, which liquid must later be separated and recycled.

The preparation of the anhydrous salt of the haloalkanoic acid is an especially troublesome problem because of the ease with which the halogen is removed by hydrolysis, thus producing the undesirable hydroxyalkanoic acid salt. Thus, the neutralization of the acid with caustic must be conducted very carefully at subnormal temperatures and the evaporation of the water therefrom must be done under vacuum at low temperatures to avoid hydrolysis.

In view of the above problems, it is an object of this invention to provide a process for making phenoxyalkanoic acids that does not require the use of an extraneous organic solvent as the reaction medium and that does not require the prior preparation of the alkali metal haloalkanoate. Other objects will appear hereinafter.

SUMMARY OF THE INVENTION

According to the invention, phenoxyalkanoic acids are made by a process comprising reacting by contacting a. a solution or dispersion of alkali metal phenate in the corresponding phenol,
b. alkali metal hydroxide and
c. haloalkanoic acid, water being continuously or intermittently removed from the reaction mixture during the reaction.

The molar ratio of phenol to phenate in (a) should be at least about 0.5, and preferably at least about 1. While there is no maximum ratio, as a practical matter, it will not ordinarily exceed about 2. If the ratio is too low, the reaction mixture becomes a thick slurry.

The molar ratio of alkali metal hydroxide to haloalkanoic acid should be at least about 1 and may be substantially higher, especially when the phenol/phenate ratio is 1 or more. The ratio should not be so high as to cause loss of fluidity in the reaction mixture, the preferred range being from about 1 to about 1.2, although it might be as high as about 1.5 when the phenol/phenate ratio is as high as 1.5 or more.

The ratio of phenate to haloalkanoic acid should be at least 1 to assure that substantially all of the latter reacts. The formation of hydroxy acid by hydrolysis of the halo acid is favored by low ratios; hence, a ratio of up to about 5 may be used, though, as a practical matter it is usually preferred to use a ratio of from about 1.1 to about 1.5.

DETAILED DESCRIPTION OF THE INVENTION

The reaction temperature is not critical and is chosen to produce a convenient rate of reaction. The rate is quite low at 80° C. and is almost instantaneous at about 160° or higher temperature. It is usually most convenient to operate the process at about 110°–150° C.

The pressure is not critical and may be atmospheric, subatmospheric or superatmospheric. It is ordinarily adjusted to provide for convenient removal of water by distillation from the reaction mixture. It is an essential feature of the invention that such water be removed either continuously or intermittently during the course of the reaction so that the water content is kept low throughout the reaction. A convenient way to effectively remove the water at a convenient temperature is to operate under a reduced pressure, such as 0.1 to 0.5 atm., though, of course, it can be distilled at atmospheric pressure. It desired, an azeotroping agent, such as toluene or chlorobenzene, can be added to facilitate removal of water and at the same time to act as an auxiliary solvent, though it is usually preferred to avoid the use of such solvents.

The alkali metal hydroxide used in the process is ordinarily NaOH because of its low price and ready availability, though KOH, LiOH and others are operable. It is most conveniently fed to the reactor as a concentrated aqueous solution, though granular, flaked or powered solid may be used if desired. The solution is most convenient for handling and metering in addition to being more quickly and easily dispersed in the reaction mixture. It is, of course, desirable to minimize the amount of water in the solution, since at least most of such water must be removed from the reaction mixture.

The phenol-phenate mixture to which the halo acid and alkali metal hydroxide are added should be substantially anhydrous. It is conveniently prepared by adding the appropriate amount of alkali metal hydroxide to an amount of phenol corresponding to the sum of the phenol and phenate desired, and then removing most of the water from the resulting mixture. The water content of the reaction mixture is preferably held below about 10%, and most preferably below about 5%.

When all the alkali metal hydroxide and haloalkanoic acid have been added to the reaction mixture and the reaction is substantially complete, the phenoxyalkanoic salt or acid is isolated by any convenient means. Suitably, the unreacted phenol is separated by vacuum distillation or solvent extraction, any inorganic salt is filtered out, and the product acid is liberated from the salt by acidification with mineral acid. Preferably, before removal of the unreacted phenol, any phenate is converted to free phenol by careful acidification of the reaction mixture with mineral acid. Excess acidity should be avoided since it would also liberate the phenoxyalkanoic acid from its salt. Optimum pH for this step varies somewhat, depending on the particular product being made, but is usually about pH 5–7. After removal of the unreacted phenol, the product salt, in the form of an aqueous solution, is further acidified with an excess of mineral acid, thus liberating the product as the free acid, in solid or liquid form depending on its melting point.

In a preferred method for isolating the product, the reaction mixture is mixed water, suitably about 1–3 volumes per volume of the mixture, the mixture is acidified as described above, the phenol is extracted with a water-immiscible solvent, suitably a hydrocarbon or halohydrocarbon such as benzene, toluene, hexane, cyclohexane, chlorobenzene, carbon tetrachloride, perchloroethylene and the like and the aqueous solution of the salt of the product acid is further acidified with mineral acid, thus precipitating the product acid. The latter is then collected, washed and, if desired, further purified by reprecipitation, recrystallization, distillation or other conventional means. The mineral acid used in the acidification steps may be any of the common ones, such as sulfuric, nitric, hydrochloric, hydrobromic or phosphoric. As a matter of economy and convenience, hydrochloric acid is preferred.

The phenols usable in the process include phenol itself, the mono- and polychloro and bromophenols, the alkylphenols wherein the alkyl groups contain up to about 5 carbon atoms and the corresponding alkylhalophenols. Specific examples include 2- and 4-chloro- and -bromo- phenols, 2,4- and 2,6-dichloro- and -dibromophenols, 2,4,5- and 2,4,6-trichloro- and -tribromophenols, the cresols and xylenols, and ar.-chloro- and -bromocresols and -xylenols.

The suitable haloalkanoic acids include the α-chloro- and α-bromoalkanoic acids, such as α-chloroacetic, α-chloropropionic, α-chlorobutyric, α-chlorododecanoic and α-chlorooctadecanoic acids and their bromo analogs and the like. The acids of most interest are those 2–4 carbon atoms.

SPECIFIC EMBODIMENTS OF THE INVENTION

The practice of the invention is illustrated by the following examples.

EXAMPLE 1

Preparation of 2,4-Dichlorophenoxyacetic Acid

Aqueous 50% sodium hydroxide, 48 g. (0.6 mole), was added 179 g. (1.1 mole) of 2,4-dichlorophenol and the temperature raised to 140° C. at atmospheric pressure while distilling off 12 g. of water and 1 g. of 2,4-dichlorophenol. During a period of 60 minutes, 47.3 g. (0.5 mole) of molten chloroacetic acid along with 40 g. (0.5 mole) of 50% sodium hydroxide were simultaneously added dropwise at 140° C. The reaction mixture was stirred an additional 45 minutes at 140° C. A total of 57.3 g. of water and 14.3 g. (0.0877 mole) of 2,4-dichlorophenol was distilled from the reaction mixture. Analysis of a reaction mixture sample for glycolic acid indicated .13% of the cloroacetic acid hydrolyzed.

The reaction mixture was diluted with 650 g. of water and acidified to pH of 5.1 with 18 g. of 37% hydrochloric acid. Extraction of the reaction mixture with tetrachloroethylene at 89° C. removed 82.1 g. (0.504 mole) 2,4-dichlorophenol and 6.7 g. (0.0304 mole) of 2,4-dichlorophenoxyacetic acid. After steaming the reaction mixture to remove 4.2 g of tetrachloroethylene, the reaction mixture was acidified with 55.9 g of 37% hydrochloric acid to a pH of -0.3 at 101° C. The molten 2,4-dichlorophenoxyacetic acid was separated and washed with 100 g. of water at 100° C. and then separated and washed with an additional 100 g. of water. The brine and water washes upon cooling and filtering gave 6.3 g. (.0285 mole) of 2,4-dichlorophenoxyacetic acid. Extraction of the brine and water wash filtrates with tetrachloroethylene gave 1.12 g. (.00507 mole) of 2,4-dichlorophenoxyacetic acid. The washed molten 2,4-dichlorophenoxyacetic acid was drained onto a glass tray and dried, 95.5 g. (.432 moles), m.p. 136°–138° C. A total of 109.6 g. (0.496 mole) of 2,4-dichlorophenoxyacetic acid was obtained from the reaction, 99.2% yield based on the chloroacetic acid. The yield based on the 2,4-dichlorophenol was 98.9%.

EXAMPLE 2

2,4-Dichlorophenoxyacetic Acid by Semi-Continuous Process

A procedure identical to Example 1 was repeated followed by four very similar runs in which the 2,4-dichlorophenol recovered in the removal of water by distillation and by extraction of the reaction mixture at pH 5 and 89° C. with tetrachloroethylene was recycled to the reactor. 2,4-Dichlorophenol was recovered as sodium 2,4-dichlorophenate from the tetrachloroethylene extract by extraction at 75° C. with 40% sodium hydroxide. Water removed by distillation and water from the washes of the molten 2,4-dichlorophenoxyacetic acid product was recycled to the reaction mixture at the end of the reaction just before adjusting the pH to 5.0. From these five cycles a total of 535.1 g. (2.42 moles) of 2,4-dichlorophenoxyacetic acid, yield 96.8% based on chloroacetic acid, was recovered. Hydrolysis of chloroacetic acid to glycolic acid was 2.0%.

EXAMPLE 3

Preparation of 2-Methyl-4-chlorophenoxyacetic Acid

Aqueous 50% sodium hydroxide, 48 g. (.6 mole), was added to 159.8 g. (1.12 moles) of 4-chloro-o-cresol. Water was distilled at atmospheric pressure from the reaction mixture along with a small amount of 2,4-dichlorophenol as the temperature of the reaction mixture was raised to 140° C. (Technical 94.2% chloroacetic acid containing 2.9% dichloroaceitc acid and 2.9% acetic acid was used in the reaction). During a period of 60 minutes, 50.2 g. (.5 mole) of chloroacetic acid, .0113 mole of dichloroacetic acid and 0.0242 mole of acetic acid along with 42.4 g. (0.53 mole) of 50% sodium hydroxide were simultaneously added dropwise at 140° C. The reaction mixture was stirred an additional 40 minutes at 140° C. A total of 54 g. of water and 7.2 g. (0.0504 mole) of 4-chloro-o-cresol were distilled from the reaction mixture.

After cooling the reaction mixture to 110° C., 255 g. of water was added and the diluted reaction mixture acidified with 15.4 g. (.124 mole) of hydrochloric acid, lowering the pH to 7.0 at 93° C. The reaction mixture was extracted with tetrachloroethylene at 93° C. in order to remove 4-chloro-o-cresol and then steamed in order to remove 9.97 g. of residual tetrachloroethylene. After adding 63.8 g. (.512 mole) of hydrochloric acid to adjust the pH of the reaction mixture to −0.3 at 102° C., molten 2-methyl-4-chlorophenoxyacetic acid was separated, washed with 100 g. of water and air-dried to give 101.1 g. of 2-methyl-4-chlorophenoxyacetic acid, m.p. 112°–116° C. This product contained 2.5% Bis-(2-methyl-4-chlorophenoxy)acetic acid, 0.66% water and 0.052% sodium chloride. The brine water layer and water wash layer cooled to 25° C. was filtered, giving 1.8 g. (0.0081 mole) of 2-methyl-4-chlorophenoxyacetic acid, m.p. 118°–119° C. The total 2-methyl-4-chlorophenoxyacetic acid recovered, correcting for 2.5% bis-(2-methyl-4-chlorophenoxy)acetic acid, sodium chloride and water, was 99.7 g. (.497 mole); yield 99.4%.

I claim:

1. In the process of making an α-phenoxyalkanoic acid by reacting an alkali metal phenate with a haloalkanoic acid, the improvement of simultaneously contacting at a temperature of at least about 80° C.
   a. a substantially anhydrous solution or dispersion of an alkali metal phenate in about one-half to 2 molar equivalents of the corresponding phenol with
   b. about 0.2 to one molar equivalent, based on the phenate, of an α-haloalkanoic acid and
   c. about one to 1.5 molar equivalents, based on the haloalkanoic acid, of alkali metal hydroxide at a temperature and pressure such that water is continuously or intermittently removed from the reaction mixture during the reaction at a rate such that the water content of the mixture does not exceed about 10 percent during the reaction.

2. The process of claim 1 wherein the halogen of the haloalkanoic acid is chlorine or bromine.

3. The process of claim 2 wherein the alkanoic acid contains 2 to about 18 carbon atoms.

4. The process of claim 1 wherein the phenol is phenol, halophenol, alkylphenol or alkylhalophenol.

5. The process of claim 1 wherein the phenol is 2,4-dichlorophenol, the alkali metal is sodium, the haloalkanoic acid is chloroacetic acid, the molar ratio of phenol to phenate is 1–2, the molar ratio of sodium hydroxide to chloroacetic acid is from 1 to about 1.5, the molar ratio of sodium 2,4dichlorophenate to chloroacetic acid is from about 1.1 to about 1.5, the reaction temperature is about 110°–150° C. and the pressure is atmospheric pressure.

* * * * *

UNITED STATES PATENT AND TRADEMARK OFFICE
CERTIFICATE OF CORRECTION

PATENT NO. : 4,035,416
DATED : July 12, 1977
INVENTOR(S) : Harry F. Brust

It is certified that error appears in the above-identified patent and that said Letters Patent are hereby corrected as shown below:

Col. 2, line 50, delete "It" and insert --If--.

Col. 2, line 60, delete "powered" and insert --powdered--.

Col. 3, line 59, after "those" and before "2-4" insert --of--.

Col. 3, line 67, after "added" and before "179" insert --to--.

Col. 4, line 11, delete "cloroacetic" and insert --chloroacetic--.

Col. 4, line 13, after "to" and before "pH" insert --a--.

Col. 4, line 48, delete the period (.) following "Water".

Col. 4, line 66, delete "dichloroaceitc" and insert --dichloroacetic--.

Col. 5, line 21, delete "Bis-" and insert --bis- --.

Col. 6, line 28, insert a hyphen ( - ) between "2,4" and "dichlorophenate", i.e., --2,4-dichlorophenate--.

Signed and Sealed this

Twenty-second Day of November 1977

[SEAL]

Attest:

RUTH C. MASON
Attesting Officer

LUTRELLE F. PARKER
Acting Commissioner of Patents and Trademarks